United States Patent [19]

Oprandy

[11] Patent Number: 5,200,312
[45] Date of Patent: Apr. 6, 1993

[54] MEMBRANE BASED DOT IMMUNOASSAY AND METHOD OF USE

[75] Inventor: John J. Oprandy, Rockville, Md.

[73] Assignee: The United States of America as represented by The Secretary of the Navy, Washington, D.C.

[21] Appl. No.: 814,160

[22] Filed: Dec. 30, 1991

Related U.S. Application Data

[63] Continuation-in-part of Ser. No. 303,191, Jan. 30, 1989, abandoned.

[51] Int. Cl.$^5$ .................. C12Q 1/70; G01N 33/545
[52] U.S. Cl. .................................. 435/5; 435/7.2; 435/7.94; 435/7.32; 435/970; 436/531; 436/810; 422/57; 427/2
[58] Field of Search ............. 435/5, 7.94, 7.2, 962, 435/970, 7.32; 436/531, 548; 427/2; 422/56, 57

[56] References Cited

U.S. PATENT DOCUMENTS

| | | | |
|---|---|---|---|
| 4,391,904 | 7/1983 | Litman et al. | 435/805 X |
| 4,774,177 | 9/1988 | Marks | 436/810 X |
| 4,797,259 | 1/1989 | Matkovich et al. | 422/101 |

OTHER PUBLICATIONS

Oprandy et al., *Am. J. Trop. Med. Hyg.* vol. 38, No. 1, pp. 87–108, (1988).
Oprandy et al., *J. Clin. Micb.*, vol. 27, No. 1, pp. 74–77, (1989).
Porter et al; Nucleic Acids Research, vol. 19, No. 14, 1991, p. 4011.
Program and Abstracts of the 40th Annual Meeting of the American Society of Tropical Medicine and Hygiene; vol. 45, No. 3, Sep. 1991.
Oprandy and Long; Journal of Clinical Microbiology, vol. 28, No. 8, Aug. 1990, pp. 1701–1703.

*Primary Examiner*—Esther L. Kepplinger
*Assistant Examiner*—Susan C. Wolski
*Attorney, Agent, or Firm*—A. David Spevack; William C. Garvert; Thomas J. Flanagan

[57] ABSTRACT

Antigens or antibodies are detected using a novel membrane based immunoassay. Known antigens or antibodies which will form complexes with antigens/antibodies to be assayed are spot filtered with pressure through a membrane. The membrane, either by itself or attached to a base material as a test strip, is incubated with a test fluid. Consequently, the resulting antibody-antigen complex is incubated directly or after an intermediate anti-antibody incubation with enzyme conjugated immunoglobulin and exposed to substrate which produces a colored insoluble product if the test target is present.

11 Claims, 2 Drawing Sheets

METHOD 1

METHOD 2

MEMBRANE BASED DOT IMMUNOASSAY AND METHOD OF USE

RELATED APPLICATION:

This application is a continuation-in-part of application Ser. No. 07/303,191 filed Jan. 30, 1989 and now abandoned.

BACKGROUND OF THE INVENTION

1. Field of the Invention

This invention relates to a rapid dot immunobinding assay. More particularly, the invention relates to a dot immunoassay in which the antigen or antibody in a clearly defined spot is bound onto a hydrophobic membrane which can be secured to a test strip.

2. Description of the Prior Art

Enzyme immunoassays (EIA) are commonly employed for the rapid diagnosis of infectious and other diseases by both antigen and antibody detection. Solid-phase formats include microtiter plate and membrane-based assays (Yolken, R. H., Yale J. Biol. Med.. 53:85-92 (1980). Successful tests have been developed for viruses (Hildreth, S. W., and Beaty, B. J., Am. J. Trop. Med. Hyg., 33:965-972 (1984); Scott, T. W. and Olson, J. G., Am. J. Trop. Med. Hyg., 35:611-618 (1986); Tsai, et al., J. Clin. Microbiology. 25:370-376 (1987) as well as bacteria and other agents (Sippel et al., J. Clin. Microbiol., 20:259-265 (1984); Beutin, et al., J. Clin. Microbiol., 19:371-375 (1984); Williams et al., J. Clin. Microbiol., 24:929-934 (1986); Smith, S. and C. F. Repetti, J. Clin. Microbiol. 25:2207-2208 (1987). Sensitivity and specificity of EIA has been shown to be comparable to fluorescent antibody (FA) (Hildreth, S. W., and Beaty, B. J., Am. J. Trop. Med. Hyg., 33:965-972 (1984)), radioimmunoassay (RIA) (Voller et al., Manual of Clinical Immunology, American Society for Microbiology, Washington, D.C. (1976)) and hemagglutination inhibition (HI) tests (Calisher et al., J. Clin. Microbiol., 24:770-774 (1986)).

In existing membrane based immunoassays, antigens and antibodies are bound to the membrane in a variety of ways, including gravity filtration and vacuum filtration. These methods as applied to hydrophobic membranes do not result in a clearly defined spot and efficient binding. Attempted solutions to this problem include modifying the hydrophobic membrane to make it hydrophilic. As a consequence, the sensitivity and practicality of the methods is not optimal. There is a need for an improved method in which binding of the antigen or antibody to a membrane gives a clearly defined spot of uniform density.

There is no mention, in the literature, of the improvement in signal-to-noise ratio by inhibiting the interaction of the test solution and the membrane. Hydrophilic membranes freely interact with test solutions and any materials, molecules, etc., contained in that solution. This causes non-specific background. Using hydrophobic membranes and achieving a balance between surface action and hydrophobicity limits undesirable backgrounds. Where hydrophobic membranes have been used before, the membrane has been wetted by solvent or surfactant prior to use.

Many viruses, such as eastern equine encephalitis (EEE) and St. Louis Encephalitis (SLE) as well as many bacteria, are significant public health threats. EEE virus infects humans and horses, frequently causing acute disease with a high rate of mortality. SLE virus is a major cause of viral encephalitis in humans. One means of combatting epidemics of these diseases is to identify a given area of high risk and subsequently control the vectors. Assaying the sera from sentinel flocks of chickens, for example, has shown to be an effective and sensitive method for arbovirus surveillance. The enzyme immunoassay (EIA) is a promising alternative to traditional assays for screening of sentinel animal sera. The technique does, however, require trained personnel to perform and read the test and specific equipment, and may take several hours to complete. For these reasons, an improved EIA is needed for field use.

SUMMARY OF THE INVENTION

Accordingly, it is an object of this invention to provide a method for detecting antigens or antibodies in fluids that may be easily and quickly performed in the field and may be performed without the use of special equipment.

It is also an object of this invention to provide a chemically stable "test strip" comprised of a hydrophobic membrane which gives a higher s/n ratio as a means to detect one or several antigens or antibodies in a rapid dot immunoassay.

Further, it is an object of this invention to provide a rapid dot immunoassay test kit, for use in the field, which has minimal backgrounds and thus improved discrimination.

In addition, it is an object of this invention to provide an improved method of binding antibodies and antigens to a hydrophobic membrane. Bound materials are referred to as "ligands".

These and additional objects of the invention are accomplished with an assay formed by spot filtering with positive pressure, antigens, or antibodies through a hydrophobic membrane to attach the ligand. The membrane, either by itself or attached to a base material as a test strip, is incubated with a test fluid suspected of containing the analyte of interest. The resulting specific antibody-antigen complex formed is detected by incubation with an indicator complex. In the case of antigen acting as ligand and antibody as the analyte (analyte being the target material in a test solution), the indicator complex could be a labeled anti-immunoglobulin specific to the species and type of the analyte. In the case of specific antibody acting as ligand and antigen as the analyte of interest, the indicator complex could be comprised of first, an antibody specific to the analyte ("second antibody"), then a labeled anti-immunoglobulin, specific to the second antibody.

A more complete appreciation of the invention will be readily obtained by reference to the following Brief Description of Drawings and Detailed Description of the Invention.

DETAILED DESCRIPTION OF THE INVENTION

Figure 1:
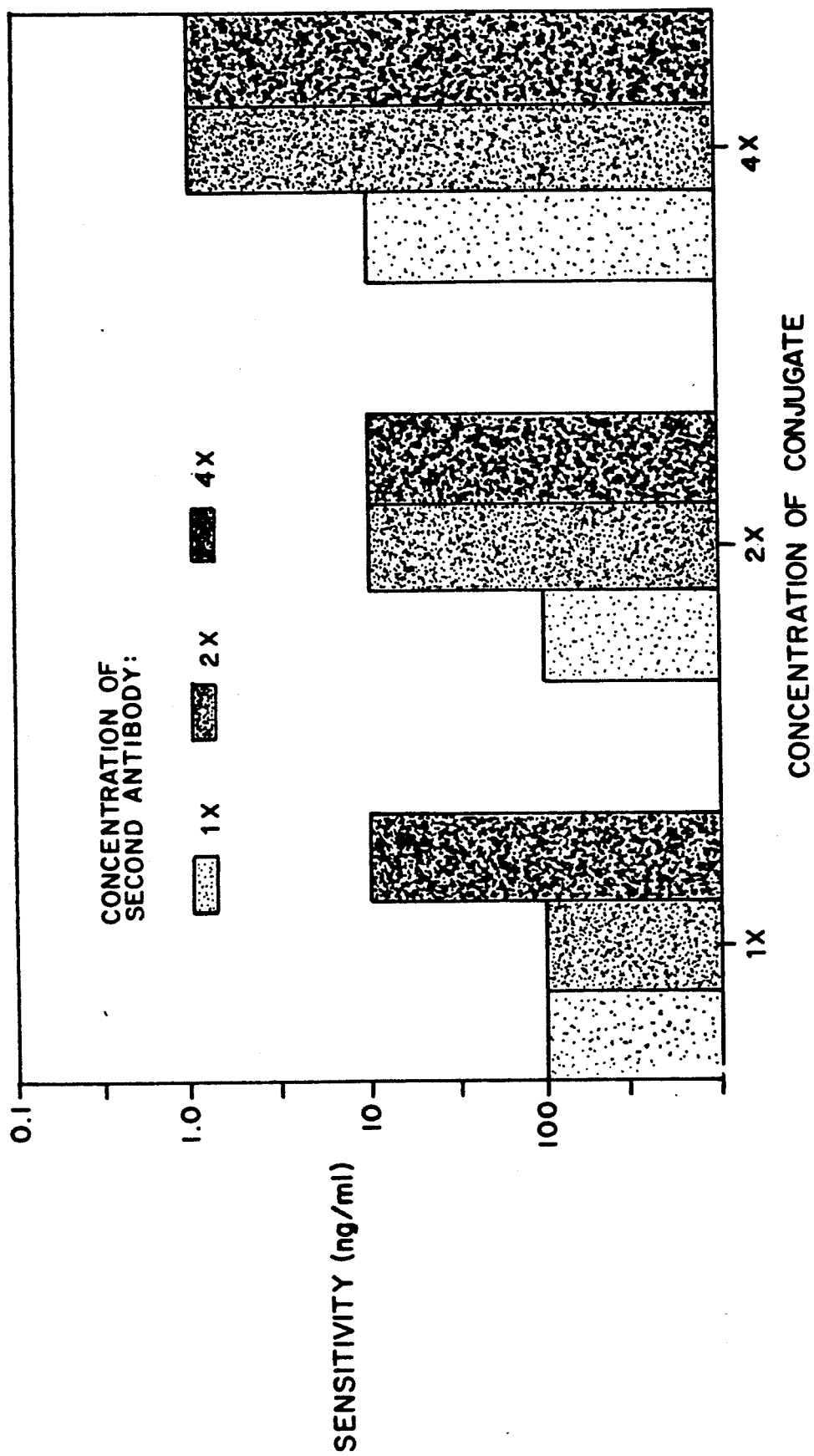
FIG. 1 shows a comparison of the effect of concentration of second antibody and enzyme conjugated antibody on sensitivity of the assay method of the invention.

The membrane required for the immunoassay must be one that allows for binding of proteins to the membrane fibers by hydrophobic interaction and/or electrostatic charges. The preferred membranes are nitrocellulose, Nylon 66 and polyvinylidene difluoride (PVDF)-IMMOBILON-P (Hydrophobic; Millipore Corp., Bedford Mass.). The most preferred membrane is PVDF. Use of a hydrophobic membrane allows ligand to bind by ionic interaction, increasing retention. The bound ligand will have hydrophilic domains which react with the analyte of interest. A buffer solution having a balance of surfactant that will allow the spotted ligand free interaction with the aqueous solution containing analyte but does not wet the membrane is a central part of the invention, and is not explained in the prior art or literature. Since the membrane retains its hydrophobic character, it does not react with molecules in the test solution; this eliminates background and allows for better discrimination of the signal because the membrane remains bright white.

The immunoassay is sufficiently catholic to be used with the antigen, the antibody, or an antigen-antibody complex connected to the membrane. The technique also permits intermediate steps known in the art such as the formation of antibody-anti-antibody complexes for greater sensitivity.

The choice of the antibody/antigen ligand to be bound onto the surface of the membrane is determined by the antigen/antibody analyte to be detected. Any test, commonly referred to as an "immunobinding assay" or "immunoassay," can be adapted to this system. The ligand must readily form an antigen-antibody complex with the analyte to be assayed and the reaction must be specific to that antigen/antibody. For this reason, monoclonal antibodies are generally preferred.

In order for the ligand to bind to the membrane, the ligand must be in solution. The preferred diluent solution for the ligand is phosphate buffered saline (PBS) or water. Water is most preferred because as the water evaporates from the PBS solution, the salt content of the PBS solution increases, possibly changing the structure of the antibodies/antigens.

The concentration of the ligand in diluent solution will vary according to the antibody/antigen used and the analyte sought after, also referred to as the test target. The concentration must be such that a good signal to noise ratio (s/n) is obtained for the assay. The preferred method is to use a box titration to determine the proper concentrations of the reactants in the assay.

Once the ligand is in solution, this solution must be filtered through the hydrophobic membrane using positive pressure. The positive pressure method gives a more clearly defined spot than is obtainable by other current methods. A clearly defined spot is one that is fairly uniform in ligand density and clearly delineated. The amount of antibody/antigen solution should be an amount that will give a uniform flow and a uniform spot of antibody. About 25 to 500 microliters of solution volume is sufficient. In the preferred embodiment of the invention, between about 50 to 200 microliters of antibody solution is filtered through the membrane. Passing about 100 microliters of ligand solution through the membrane is most preferred.

Any apparatus that provides a means of filtering a solution through the membrane with positive pressure and which can be hermetically sealed to the membrane can be used. This type of apparatus should provide a laminar flow of antibody solution and no dispersion of antibody beyond the desired spot. Preferably, a plastic or O-ring sealed apparatus held by force against the membrane is used for the invention. A polypropylene syringe placed atop the membrane, cushioned by filter paper, is sufficient. The pressure technique is described in related application Ser. No. 07/519,072 now U.S. Pat. No. 5,039,493 issued Aug. 13, 1991.

The ligand solution is filtered through the membrane at an even rate. This causes the antibody/antigen to bind to the membrane. At this point, the antibody/antigen will not be completely bound to the membrane. The membrane must dry in order for the antibody/antigen to bind completely. The best method is to simply air dry the membrane with bound antibody/antigen for about an hour. Once dried, the resulting antibody/antigen-bound membrane may be stored for later use.

The particular choice of whether the test target is an antigen or an antibody creates several alternative embodiments based on the same principles. In the first embodiment, an antigen is the test target. Here, an antibody (specific to the antigen) is filtered through the membrane. In the second embodiment, an antibody is the test target. Here, the antigen (specific to the antibody) is filtered through the membrane. In the third embodiment, an antibody is a test target. An antibody specific to an antigen which in turn is specific to the test target is be filtered through the membrane. The antigen is then incubated with the bound antibody. In both the second and third embodiment, an antigen specific to the test target is exposed on the membrane. The third embodiment is preferred for antibody assay over the second embodiment because the third embodiment has greater sensitivity and specificity.

Before using the antibody/antigen-bound membrane to detect test targets, all non-specific binding sites on the antigen/antibody-bound membrane must be blocked so that test targets bind to the antibody/antigen rather than to the membrane. Various blocking agents that will prevent the non-specific binding of biological molecules to membranes are available, such as various non-fat dry milk preparations ("BLOTTO") or gelatin. In the preferred embodiment of the invention, non-fat dry milk, Carnation brand to be exact, is the blocking agent. Since the dry antibody/antigen-bound spot must be rewetted for assay use, one can combine the wetting agent and blocking agent in a single blocking/wetting solution. This solution is comprised of the blocking agent and a surfactant in a buffer. Any surfactant may be used, although TWEEN 20, a wetting agent (surfactant), is preferred. The preferred buffer is PBS or Tris buffered saline. The blocking/wetting solution must contain enough blocking agent and surfactant in the buffer so that all non-specific binding sites on the antibody/antigen-bound membrane are blocked and the hydrophobicity of the antibody/antigen-bound spot is reduced. A solution of about 2 to 5% non-fat dry milk and about 0.01 to 0.1% TWEEN 20 in PBS is preferred, with a TWEEN 20 concentration of about 0.02% being most preferred. This is much lower than in conventional microtitre plate based assays and serves to wet the reagent spot while not diminishing the hydrophobicity of the membrane per se.

If desired, the blocking step may be completed and the membrane dried and stored. If this is done, the dry blocked antibody/antigen-bound spot must be rewetted briefly with a wetting solution. This wetting solution is the blocking/wetting solution referred to earlier but without the blocking agent. The end result is a wetted blocked antibody/antigen-bound spot and membrane, which can be cut into a test strip for use in an assay.

The test strip may be comprised of a base material upon which the blocked antibody/antigen membrane may be attached. Alternatively the blocked antibody/antigen membrane may be used as a test strip in itself. The base material must not be reactive with the blocked antibody/antigen membrane.

Any fluid may be assayed for test targets using the test strip. This fluid can be an aqueous sample such as suspect contaminated water or seawater, a sample extracted from a material or a body fluid. Serum and Cerebrospinal fluid (CSF) are two examples. Although body fluids may be assayed "as is", in the preferred embodiment of the invention, any body fluid is diluted to about 1:5 with a buffer/surfactant solution. Of course, the buffer/surfactant can be used to extract body fluid samples from materials such as fabrics, paper, etc. The choice of buffers and surfactants is the same as for the blocking/wetting solution. However, a concentration of 0.01 to 0.08% TWEEN 20 is preferred for the buffer/surfactant solution, with a TWEEN 20 concentration of 0.02% being most preferred.

Whether or not the body fluid is diluted, a blocking agent should be added to the fluid prior to the assay. The blocking agent concentration in the final fluid solution should be about 2%. If the body fluid is diluted or extracted from a sample, the blocking agent can be added to the buffer/surfactant solution.

The test strip must be incubated with the fluid for a time sufficient to allow the suspected test target to react and form antigen-antibody complexes with the antibodies/antigens bound on the test strip. Generally, about 1 minute to two hours is sufficient time for this incubation period. After incubation, the reacted test strip is washed for the purpose of reducing the concentration of excess antigens/antibodies that might interfere with later assay steps, giving a false reading. The strips are washed in the buffer/surfactant solution for about 10 to 90 seconds. In the preferred embodiment of the invention, the wash time is about 30 seconds.

As previously stated, the particular choice of whether the test target is an antigen or an antibody creates several alternative embodiments based on the same principles. At this point in the invention, the method of the second and third embodiments continues with an incubation with an enzyme-conjugated immunoglobulin. However, in the case of the first embodiment, two paths can be followed. The invention may proceed with the enzyme-conjugated immunoglobulin or, in an alternative embodiment designated the fourth embodiment, subjected to an intermediate incubation. In this fourth embodiment, the reacted test strips are incubated with an antibody that is reactive with the suspected antigen that complexed with the antibody bound to the test strip. Generally, any antibody that forms an antigen-antibody complex with the complexed antigen may be used, but a polyclonal antibody is preferred. As polyclonals have more binding sites, they increase the signal to noise ratio for the assay. The time for this intermediate incubation may be the same as that for the first, and the reacted test strips are again washed with the buffer/surfactant solution.

In all embodiments of the invention, the reacted test strip is next incubated with a labeled specific immunoglobulin. In the case of the second, third, and fourth embodiments, this immunoglobulin must be an immunoglobulin type specific anti-antibody since it will be reacting with an antibody. However, the first embodiment requires an antibody since it must react with an antigen. The anti-antibody or antibody, as the case may be, is an immunoglobulin that forms a complex by specific binding with the antibody/antigen from the previous step. The label that the immunoglobulin is conjugated with can be an enzyme that will react with a selected substrate. The preferred labels are enzymes such as horseradish peroxidase, urease, alkaline phosphatase and glucose oxidase. In the most preferred embodiment of the invention, horseradish peroxidase is the enzyme of choice.

The time for this second incubation is about the same as that for the first incubation. The reacted test strips are again washed as after the first incubation, but the strips must then be washed in a buffer solution, using the buffer previously described. It is important that the reacted strips be washed in buffer prior to the final incubation since excess surfactant may inhibit certain enzyme substrates.

The final incubation is with a substrate solution. The substrate must be one that reacts with the enzyme to form a colored insoluble product. The preferred substrates for peroxidase are 4-chloro-1-naphthol or Tetramethyl benzidine (TMB). TMB is most preferred. The incubation time should be long enough for the substrate and enzyme to reach maximum reaction. Generally, about five minutes is sufficient time for TMB.

After this final incubation, the strip is examined. If there is a detectable color (by eye or machine) on the test strip, the assay is positive for the suspected antigen/antibody. Conversely, a sample yielding essentially no color is considered negative.

A test kit for field use comprises the proper test strip, wetting solution, washing solution, buffer/surfactant solution, buffer solution, enzyme conjugated immunoglobulin solution, and substrate as well as containers for carrying out the dilutions and incubations.

Having generally described the invention, the following examples are given to illustrate specific applications of the invention. These specific examples are not intended to limit the scope of the invention described in this application.

EXAMPLE I

Detection of a polysaccharide by immunobinding assay using hydrophobic PVDF (Oprandy and Sippel, *J. Clin. Microbiol.*, 27:74-77 (1989)). This work illustrates the improved sensitivity of the hydrophobic PVDF assay system. The reference cited did not, however, explain the importance of a balance between surface action and hydrophobicity.

*N. meningitidis* polysaccharide groups A and C were obtained from the American Type Culture Collection (Rockville, Md.).

An IgG mouse monoclonal antibody (#1622) to meningococcal group A polysaccharide was generously provided by H. Feindt (Hynson, Wescott and Dunning, Baltimore, Md.). Hyperimmune rabbit sera to *N. meningitidis* polysaccharide group A was purchased from Difco, Inc. (Detroit, Mich.).

Assays were performed on PVDF membranes (IMMOBILON-P, Millipore Corp., Bedford, Mass.). One microgram of antimeningococcal group A monoclonal antibody (#1622), in 100 microliters of sterile distilled water, was spot filtered by pressure through the membrane. Treated membranes were then allowed to dry at room temperature for at least one hour. These membranes were wetted in a solution of PBS with 0.1% TWEEN-20 and then non-specific binding sites were blocked by incubating the membrane in a solution of 5% non-fat dry milk (NFDM) in PBS/0.01% TWEEN-20 for 1 h at room temperature. Prepared membranes could be dried and stored at 4 degrees C., at this point for later use. Such membranes had to be re-wetted before use by immersing them in a solution of PBS/0.01% TWEEN-20, prior to initiating the assay.

Assays were performed by dipping PVDF strips, spotted with monoclonal antibody, into microcentrifuge tubes containing 100 microliters meningococcal polysaccharide in a diluent of PBS/0.01% TWEEN/1% NFDM. Concentrations of antigen ranged from 10 pg/ml to 100 ng/ml in 10-fold increments. After this first incubation, membrane strips were washed in PBS/0.01% TWEEN for 1 min. The second incubation was with anti-meningococcal group A rabbit serum and the strips were washed again. PVDF strips were incubated with peroxidase-conjugated anti-rabbit IgG (Kirkegaard and Perry Laboratories) for 1 h at 37° C. PVDF strips were then washed as before and placed in a final wash of PBS for 1 min. After this, assay strips were placed in a substrate solution of 4-chloro-1-naphthol and color development allowed to occur for approximately 30 min at 37° C. All assays were repeated at least three times. A negative sample yielded essentially no color on the membrane, positives were judged as a sample yielding a detectable (by eye) color.

Length of incubation, at a constant temperature of 37° C., was varied for antigen in one group of assays and for both antigen and second antibody (rabbit) for another set of assays. Incubation temperature, for 1 h incubation periods, was varied for both antigen and second antibody in another experiment. Incubation with conjugate was constant for 1 h at 37° C. for both of the above experiments. In a final experiment, incubation times for all steps were reduced to 5 min (incubation in substrate was for 15 min) and performed at room temperature. To increase sensitivity in this assay, second antibody (rabbit serum) and enzyme-conjugate concentrations were increased two-fold and four-fold. Antigen concentrations were as above. The results of this increase are shown in FIG. 1.

EXAMPLE II

Detection of antibody by immunobinding assay using hydrophobic PVDF membranes (Oprandy et al., *Am. J. Trop. Med. Hyg.*, 38:181-186 (1988)).

Inactivated eastern equine encephalomyelitis (EEE) and St. Louis Encephalitis (SLE) antigens were obtained from the Reference Center for Arthropod-Borne Viruses, Yale University, New Haven, Conn. This material had been prepared as sucrose-acetone extracted virus-infected suckling mouse brain. Lyophilized material (0.25 g) was reconstituted in 1.0 ml phosphate buffered saline (PBS), pH 7.4.

Chickens were obtained from Truslow Farms, Chestertown, Md. At 6 days of age, chicks were divided into four groups of six birds each. One group was inoculated with 0.9 ml diluent (cell culture medium with 20% heat-inactivated Fetal Calf Serum (FCS)) as a control. Birds in the remaining three groups were inoculated intramuscularly with $10^{3.8}$ TCID$_{50}$ EEE virus, $10^{3.3}$ TCID$_{50}$ SLE virus, or $10^{3.8}$ TCID$_{50}$ Highland's J (HJ) virus. "TCID$_{50}$" represents Tissue Culture Infectious Dose 50. Virus strains, bleeding procedures, and processing of blood are the same as described by Scott and Olson (*Am. J. Trop. Med. Hyg.*, 35:611-618 (1986)).

Sentinel flocks of chickens were maintained in Prince Georges, Anne Arundel, Baltimore, Wicomoco, and Worcester counties, Maryland. These birds were bled once a week or every other week. Blood was collected and processed as described above.

All steps of the immunoassay were performed at room temperature (22-25 degrees C.). Optimal serum, antigen, and conjugated dilutions were determined by box titrations. Serum controls were normal chicken sera and antigen controls were sucrose-acetone dried uninfected mouse brain at dilutions equivalent to those of the material tested.

Assays were done on a hydrophobic PVDF membrane (IMMOBILON-P, Millipore Corp. Bedford, Massachusetts). Virus infected suckling mouse brain preparations were diluted 1:25 in PBS (pH 7.4) and then spotted onto a PVDF membrane. Spotting was achieved by placing a 1 ml tuberculin syringe onto the membrane and injecting 50 microliters of the antigen preparation through it. The membrane was then allowed to dry at room temperature for at least 1 hour. The hydrophobic membrane was wetted in a solution of PBS with 0.2% TWEEN 20 and then nonspecific binding sites were blocked by incubating the membrane in a solution of 5% nonfat dry milk in distilled water for 15 min. Prepared membranes were then dried and stored at 4 degrees C. for later use. Membranes that had been stored were rewetted before use by immersing them in a solution of PBS/0.01% TWEEN-20, prior to initiating the assay.

Assays were performed by dipping PVDF strips with antigen dots into microcentrifuge tubes containing 50 microliters of serum diluted 1:10 with PBS containing 0.05% TWEEN 20 and 2% bovine serum albumin (BSA). Incubation was for 15 minutes. PVDF strips were then washed by placing them in a container with 50-100 ml of wash solution (PBS/0.05% TWEEN 20) and gently agitated for 5 minutes. After washing, PVDF strips were incubated with peroxidase-conjugated anti-chicken IgG for 15 minutes. PVDF strips were then washed as before and placed in a final wash of distilled water for 1 min. PVDF strips were then placed in a substrate solution of 4-chloro-1-naphthol and color development allowed to occur for approximately 10 min. Samples were scored qualitatively by eye from no reaction (0) to maximal color development (+4).

EXAMPLE III

Pressure blotting vs. Wetted membrane adsorption

Figure 2:
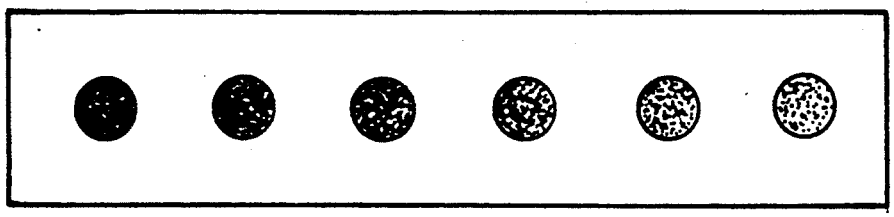
FIG. 2 shows the difference in the ability of the test system to generate signal by pressure blotting and passive adsorption.
Figure 2:
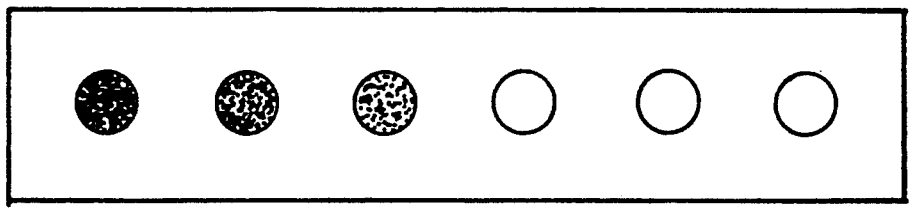

In an experiment to determine the efficiency of binding to hydrophobic PVDF, an equivalent mass of mouse immunoglobulin (IgG) was immobilized on PVDF by two methods. Method 1 spot filtered the solution containing IgG by positive pressure; method 2 rendered the membrane hydrophilic by immersion in methanol, followed by equilibration in aqueous buffer and then applied the mouse IgG by drops. The membranes were then blocked and incubated with antimouse IgG labeled with peroxidase. After washing, the membrane strips were incubated with tetramethyl benzidene substrate and a colored spot appeared. The results are shown in FIG. 2.

Six two-fold dilutions were made of the mouse IgG, from 1/1000 to 1/32000.

Visible color was observed in all six spots on the pressure blotted membrane strip. This indicated that a dilution of 1/32000 of IgG was detectable. In contrast, spots on the wetted membrane strip were only observed for the two lowest dilutions (highest concentrations).

Pressure blotting of protein onto dry hydrophobic PVDF (IMMOBILON-P, Millipore Corp., Bedford Mass.) for later immuno-detection was a superior method as compared with passive adsorption into "wetted" PVDF. The detectable level of ligand on the membrane was eight times greater using the pressure blot technique.

Obviously, many modifications and variations of the present invention are possible in light of the above teachings. It is therefore to be understood that within the scope of the appended claims, the invention may be practiced otherwise than as specifically described.

What I claim is:

1. A test strip for use in an aqueous immunobinding assay made by the method comprising:

filtering an aqueous solution containing a ligand selected from the group consisting of an antigen, antibody, and antigen-antibody complex, under positive pressure through a hydrophobic polyvinylidene difluoride (PVDF) membrane to form a clearly defined spot;

immobilizing said ligand by drying said membrane.

2. A test strip as described in claim 1 wherein the said ligand is an antigen.

3. A test strip as described in claim 1 wherein the said ligand is an antibody.

4. A test strip as described in claim 1 wherein the said ligand is an antigen-antibody complex.

5. A test strip as described in claim 2 wherein said antigen is eastern equine encephalomyelitis virus.

6. A test strip as described in claim 2 wherein said antigen is St. Louis encephalitis virus.

7. A test strip as described in claim 3 wherein said antibody is an IgG mouse monoclonal antibody to meningococcal group A polysaccharide.

8. A method for making a test strip for use in an aqueous immunobinding assay comprising:

filtering an aqueous solution containing a ligand selected from the group consisting of an antigen, antibody, and antigen-antibody complex, under positive pressure through a hydrophobid PVDF membrane to form a clearly defined spot; and immobilizing said ligand by drying said membrane.

9. An aqueous immunobinding assay method for detecting an antigen or antibody target in a test solution comprising:

filtering an aqueous solution containing a ligand which specifically binds to said target wherein said ligand is selected from the group consisting of an antigen, antibody, and antigen-antibody complex, under positive pressure through a hydrophobic PVDF membrane to form a clearly defined spot;

p1 immobilizing said ligand by drying said membrane to form a test strip;

incubating said test strip in a blocking/wetting solution comprising a blocking agent in a wetting solution, wherein the amount of said blocking agent is sufficient to block all non-specific binding sites and said wetting solution comprises a surfactant in a buffer, wherein the amount of said surfactant is sufficient to reduce the hydrophobicity of said clearly defined spot;

diluting said test solution in said wetting solution and incubating said test strip therein for a time sufficient for any target present to bind to said ligand and form a reacted test strip;

incubating said reacted test strip with a label conjugated to an antigen or antibody which specifically binds to said target; and measuring said label to determine if said target is present.

10. The method according to claim 9 wherein said label is conjugated to an antibody and said label is selected from the group consisting of horseradish peroxidase, urease, alkaline phosphatase, glucose oxidase, and fluorescent molecules.

11. The method according to claim 10 wherein said label is horseradish peroxidase and its substrate is selected from the group consisting of 4chloro-1-naphthol and tetramethyl benzidine.

* * * * *